United States Patent [19]

Johnson

[11] Patent Number: 5,343,043
[45] Date of Patent: Aug. 30, 1994

[54] REMOTE SENSOR DEVICE FOR MONITORING MOTOR VEHICLE EXHAUST SYSTEMS WITH HIGH SPEED SAMPLING

[75] Inventor: James H. Johnson, Woodstock, Ill.

[73] Assignees: Envirotest Syst. Corp., Tucson, Ariz.; Colorado Seminary, Denver, Colo.

[21] Appl. No.: 120,069

[22] Filed: Sep. 13, 1993

Related U.S. Application Data

[63] Continuation of Ser. No. 45,211, Apr. 13, 1993.

[51] Int. Cl.$^5$ .................... G01N 21/61; G01N 21/25; G01N 21/01
[52] U.S. Cl. ............................ 250/338.5; 250/339.01; 250/347; 356/438
[58] Field of Search ...................... 250/338.5, 339, 340, 250/341, 343, 347, 345, 349, 236; 356/437, 438, 439; 359/216, 217, 226

[56] References Cited

U.S. PATENT DOCUMENTS

| | | | |
|---|---|---|---|
| 3,696,247 | 10/1972 | McIntosh et al. | 250/339 |
| 3,958,122 | 5/1976 | Jowett et al. | 250/346 |
| 3,973,848 | 8/1976 | Jowett et al. | 356/51 |
| 4,126,396 | 11/1978 | Hartmann et al. | 356/434 |
| 4,160,373 | 7/1979 | Fastaia et al. | 73/23 |
| 4,348,732 | 9/1982 | Kreft | 364/571 |
| 4,390,785 | 6/1983 | Faulhaber et al. | 250/330 |
| 4,490,845 | 12/1984 | Steinbruegge et al. | 382/1 |
| 4,678,914 | 7/1987 | Melrose et al. | 250/343 |
| 4,924,095 | 5/1990 | Swanson, Jr. | 250/338.5 |
| 5,210,702 | 5/1993 | Bishop et al. | 250/338.5 X |
| 5,252,828 | 10/1993 | Kert et al. | 250/338.5 X |

OTHER PUBLICATIONS

*IR Long-Path Photometry: A Remote Sensing Tool for Automobile Emissions,* Bishop et al., Departments of Chemistry & Physics, University of Denver, Denver, Colo. Analytical Approach, American Chemical Society, Analytical Chemistry, 1989., 61 671A.

Primary Examiner—Constantine Hannaher
Assistant Examiner—Edward J. Glick
Attorney, Agent, or Firm—Cooper & Dunham

[57] ABSTRACT

Apparatus for detecting and measuring relative concentrations of pollutants such as HC, CO and $CO_2$ in the exhaust emissions from passing vehicles includes an infrared (IR) beam source for directing an IR beam through a vehicle's exhaust plume and a detector disposed on one side of a roadway and a lateral transfer mirror (LTM) disposed on the other side of the roadway for lateral reflecting of the IR beam back through the vehicle's exhaust plume and onto the detector. The LTM allows for close spacing and precise alignment between the emitted and reflected beam paths and permits the IR beam source and detector to be disposed in a single module. Compensation for variation in a range of vehicle operating conditions is provided by adjustable, computer-controlled potentiometers, while audio and/or visible light feedback of the detected IR signal allows a single operator to precisely align the optical components of the apparatus. The IR detector module includes a rotating mirror arrangement for directing the reflected IR beam in a pulsed manner onto a plurality of spaced detector elements, each adapted for detecting a specific pollutant, with the detector elements calibrated with each detected IR pulse to reduce errors arising from circuit drift.

6 Claims, 6 Drawing Sheets

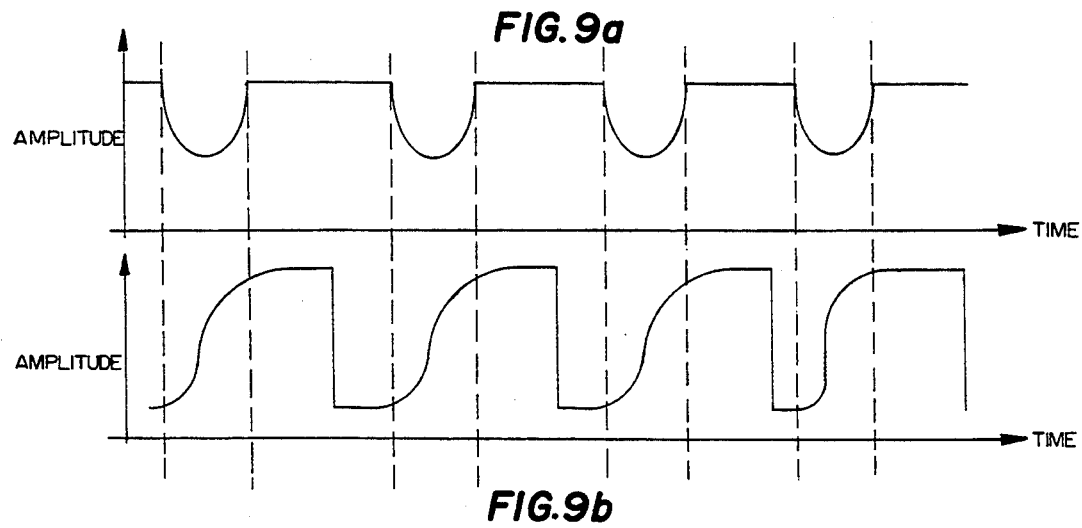
FIG. 9a
FIG. 9b
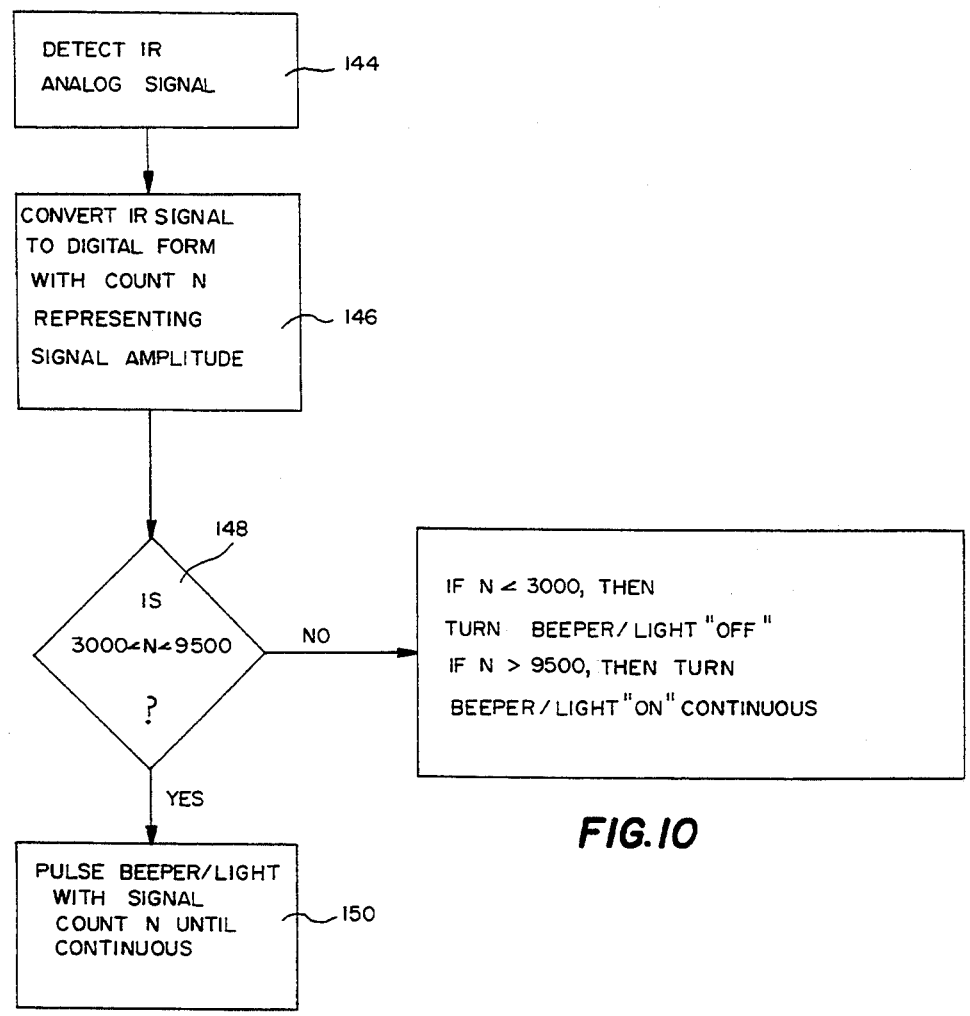
FIG. 10

5,343,043

REMOTE SENSOR DEVICE FOR MONITORING MOTOR VEHICLE EXHAUST SYSTEMS WITH HIGH SPEED SAMPLING

RELATED APPLICATION

This is a continuation of application Ser. No. 08/045,211, filed Apr. 13, 1993.

FIELD OF THE INVENTION

The present invention relates to the monitoring and detection of vehicle emitted pollutants. The invention has particular application to monitoring the exhaust emissions of motor vehicles under actual operating conditions.

DESCRIPTION OF THE PRIOR ART

Detecting and limiting environmental pollution has become an area of the utmost importance to industrialized societies. Substantial effort and resources have been committed to detecting and curbing sources of industrial pollution in all forms. One of the major contributors to air pollution is the internal combustion engine which is used to power motor vehicles. It is highly desirable to measure exhaust emissions from a vehicle under actual operating conditions and not in a static situation such as while idling at low RPM. Dynamic testing under actual operating conditions not only provides a more accurate indication of pollutant emissions, but also makes vehicle tampering for the purpose of circumventing the pollution test equipment virtually impossible.

Pollution monitoring systems for remotely measuring vehicle emissions have been proposed. U.S. Pat. No. 4,924,095 discloses a remote gas analyzer for motor vehicle exhaust emission surveillance in which a planar array of gas analyzer beams intersects substantially an entire cross-sectional segment of the exhaust gas plume in order to determine the volume concentration of first gas pollutants in the exhaust of a motor vehicle passing the array. These first pollutants have a relatively high and more easily detectable concentration. A second, multi-spectral gas analyzer beam intersects the exhaust to determine the change in concentration of the less prevalent pollutants with respect to ambient, and also determines the change in concentration of the first pollutants. The gas analyzer beams transit the exhaust gas plume in a first path and are then reflected back through the plume in a second path by a matrix array of retro-reflectors.

Another approach for analyzing vehicle emissions is disclosed in U.S. Pat. No. 5,210,702, issued May 11, 1993, for remote detecting, measuring and recording of $NO_x$, $CO$, $CO_2$, $HC$ and $H_2O$ levels from the exhaust of moving motor vehicles. An optical mechanism splits an infrared (IR) beam into two to four components, and devices are positioned for receiving each of the IR components and generating two to four signals indicative of, for example, $CO$, $CO_2$, $HC$ and $H_2O$. An IR source and the receiving mechanism are aligned on opposite sides of a roadway and a visual recording device is positioned for visually recording the vehicle and test results. The IR beam makes a single pass across the roadway through the vehicle's exhaust plume between the IR source and detector. A polygon-shaped rotating mirror reflects the IR beam after passing through the vehicle's exhaust plume onto a plurality of detectors, each adapted to measure the concentration of a respective pollutant. Still another approach disclosed in patent application, Ser. No. 07/895,342, filed Jun. 8, 1992, employs a pair of spaced planar mirrors for reflecting the emitted IR beam back across the roadway to the detector.

Even when monitoring vehicle exhaust emissions under actual operating conditions, operating limitations of the gas analyzer introduce measurement inaccuracies. For example, typical IR detectors are highly temperature sensitive and exhibit increased resistivity with decreasing temperature. An IR detector typically provides a maximum output at $-70°$ C. Thermo-electric coolers capable of reducing the temperature of a detector $21°$ C. below ambient are used to improve detector signal-to-noise (S/N) ratio. By running the coolers at maximum power, the detected signal level may be increased. Some prior art gas analyzers utilize a number of manually adjustable potentiometers to improve the S/N ratio by tuning the detector circuit for operation at a given temperature. In addition, the latent heat absorbed by metal components adjacent to the beam detector when the beam is incident upon the detector gives rise to differential heating and cooling rates which also reduce measurement accuracy. Finally, prior art approaches have suffered from difficulty in aligning the optical components on opposite sides of the roadway which also limits the accuracy and sensitivity of the gas analyzer measurements.

SUMMARY OF THE INVENTION

It is a general object of the invention to provide an improved vehicle emissions monitoring apparatus for roadside use which avoids the disadvantages of prior approaches while affording additional structural and operating advantages.

An important feature of the invention is the use of a unitary lateral transfer mirror on one side of a roadway in combination with an IR beam source and detector on the other side of the roadway which facilitates alignment of the optical elements in the vehicle emissions monitoring apparatus.

Another important feature of the invention is the use in a roadside vehicle emissions monitoring apparatus of an improved IR beam source and detector employing a plurality of adjustable, computer-controlled potentiometers for compensating for temperature variation and a high speed IR beam sampling arrangement which allows for high frequency re-calibration of the IR detector to reduce errors caused by circuit drift.

In connection with the foregoing features, it is another feature of the invention to facilitate optical alignment of an IR beam-based vehicle emissions monitoring apparatus in the field such as at roadside by providing a system operator with either a pulsed light beam or pulsed audio signal, where the pulse frequency represents the magnitude, or strength, of the received IR beam.

In summary, there is provided apparatus for high speed detection of pollutants in an exhaust plume of a motor vehicle, wherein an IR beam is directed through the exhaust plume and interacts with the pollutants, the apparatus comprising: optical means including a rotating mirror for receiving the IR beam after transit through the exhaust plume, wherein the rotating mirror includes N reflecting side walls and rotates at an angular velocity V; a plurality of IR detectors each adapted to detect a specific pollutant in the exhaust plume, wherein the IR detectors are arranged in a spaced array adjacent to the rotating mirror and adapted to receive the IR beam reflected from the side walls of the rotating mirror, wherein the IR beam reflected from one of the side walls of the rotating mirror is sequentially directed onto each of the detectors and wherein each of the IR detectors receives the IR beam as a series of IR pulses; and digital timing means coupled to the rotating mirror and responsive to the angular velocity V thereof and further coupled to each of the IR detectors for actuating the IR detectors in a timed manner, wherein each of the IR detectors samples the IR beam upon receipt of an IR pulse at predetermined time intervals determined by the angular velocity V of the rotating mirror.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages, of the present invention.

BRIEF DESCRIPTION OF THE DRAWINGS

For the purpose of facilitating an understanding of the invention there is illustrated in the accompanying drawings a preferred embodiment thereof, from an inspection of which, when considered in connection with the following description, the invention, its construction and operation, and many of its advantages should be readily understood and appreciated.

FIGS. 9a and 9b are respectively graphic illustrations of the variation of received IR signal amplitude and the integration of the received IR signal by IR signal processing circuitry in the remote sensor device over time; and FIG. 10 is a simplified flow chart illustrating the steps carried out by IR signal detection circuitry for providing an audio and/or video signal for optical alignment of the remote sensor device.

DESCRIPTION OF THE PREFERRED EMBODIMENT

Figure 1:
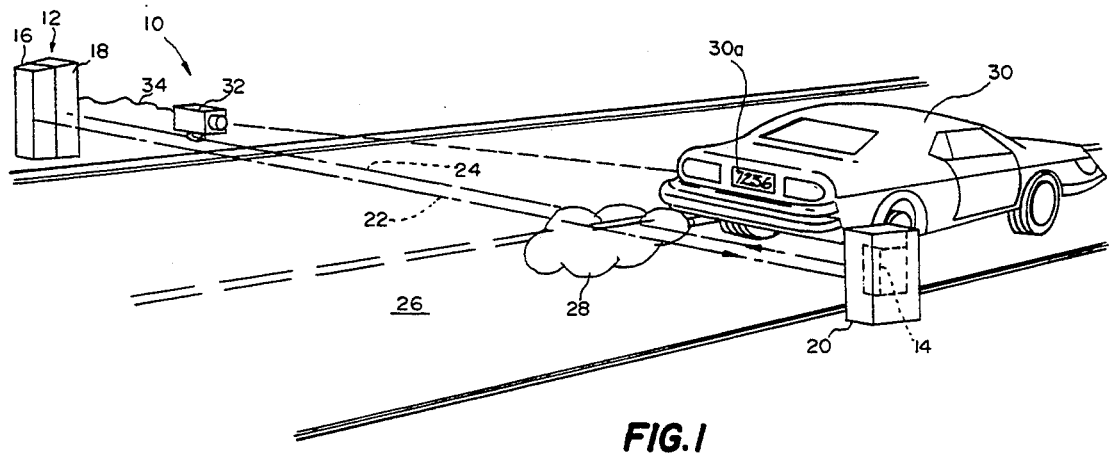
FIG. 1 is a simplified schematic diagram of a remote sensor device for monitoring motor vehicle exhaust emissions in accordance with the present invention.

Referring to FIG. 1, there is shown a simplified schematic diagram of a motor vehicle exhaust emission monitoring system 10 in accordance with the principles of the present invention. The exhaust emission monitoring system 10 is designed for non-intrusive measurement of vehicular emission by generating and monitoring an IR beam emitted and reflected approximately 10-18 inches above a roadway. Gasoline powered vehicles drive through the beam and their exhaust "interferes" with the transmission of the IR beam and appropriate detectors measure and calculate the CO, HC and $CO_2$ vehicular emissions and provide a digitized video picture of the rear of the vehicle including its license plate.

Figure 2:
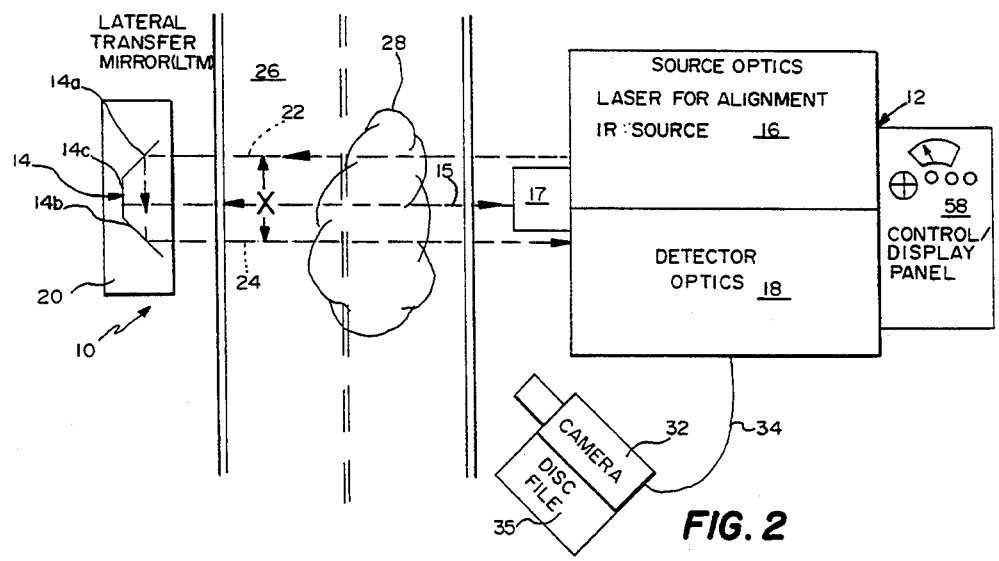
FIG. 2 is a combined schematic and block diagram of the remote sensor device for monitoring motor vehicle exhaust emissions of FIG. 1.

With reference to FIG. 1 as well as to FIG. 2, which is a simplified plan view in schematic and block diagram form of the exhaust emission monitoring system 10, a motor vehicle 30 travelling along a roadway 26 passes between a gas analyzer 12 and a lateral transfer mirror (LTM) 14 disposed on opposing sides of the roadway. Gas analyzer 12 includes a source optics module 16 and a detector optics module 18. The source and detector optics modules 16, 18 include a laser for aligning the source and detector optics with the LTM 14 prior to use. The source optics module 16 includes an IR source for emitting an IR beam which is 6 inches in diameter in a particular embodiment. The IR source emits an IR beam 22 across roadway 26 and onto a first reflecting surface 14a of the LTM 14. LTM 14 is disposed in and supported by a housing 20. The incident IR beam 22 is reflected from the LTM's first reflecting surface 14a onto a second reflecting surface 14b. The second reflecting surface 14b directs the reflected IR beam 24 back across the roadway 26 and onto the detector optics module 18 of the gas analyzer 12. As vehicle 30 travels along roadway 26, the IR beam is interrupted by the vehicle's chassis and is then transmitted through the vehicle's exhaust emission plume 28 which trails the vehicle. At the same time, a video camera 32 connected to the gas analyzer 12 via a cable 34 takes a photograph of the aft portion of vehicle 30 including its license plate 30a. This provides an operator of the exhaust emission monitoring system 10 with a permanent record of the identity of the vehicle and the exhaust emission being monitored. The gas analyzer 12 further includes an operator's control/display panel 58 including an arrangement of control elements and displays.

Video camera 32 in one embodiment is of the digital type to provide a digitized still image video picture of the vehicle's license plate 30a as the IR beam is directed through its exhaust plume 28. The digital image may then be stored on a disc file 35 in digital form for use by computers and computerized equipment.

Disposed intermediate and coupled to the first and second reflecting surfaces 14a, 14b of the LTM 14 is a third generally planar panel 14c. The two reflectors 14a, 14b and the planar panel 14c disposed therebetween form an integral structure to facilitate alignment of incident and reflected IR beams 22, 24 with source and detector optics modules 16, 18. Planar panel 14c is comprised of milled aluminum in one embodiment and may be used as a target for laser beam 15 for aligning the source and detector optics modules with the LTM 14. The laser beam source and detector 17 is thus used in combination with planar panel 14c of the LTM 14 for gross alignment of the optical elements of the motor vehicle exhaust emission monitoring system 10.

Figure 3:
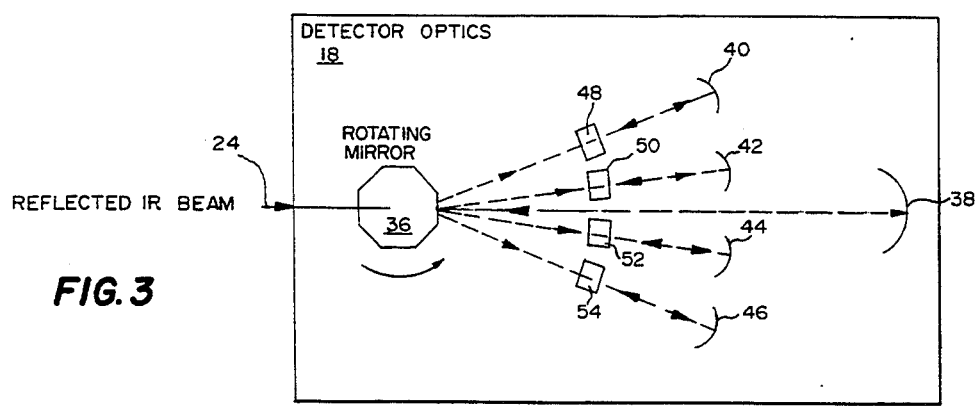
FIG. 3 is a plan view of the detector optics used in the remote sensor device for monitoring motor vehicle exhaust emissions of FIG. 1.
Figure 4:
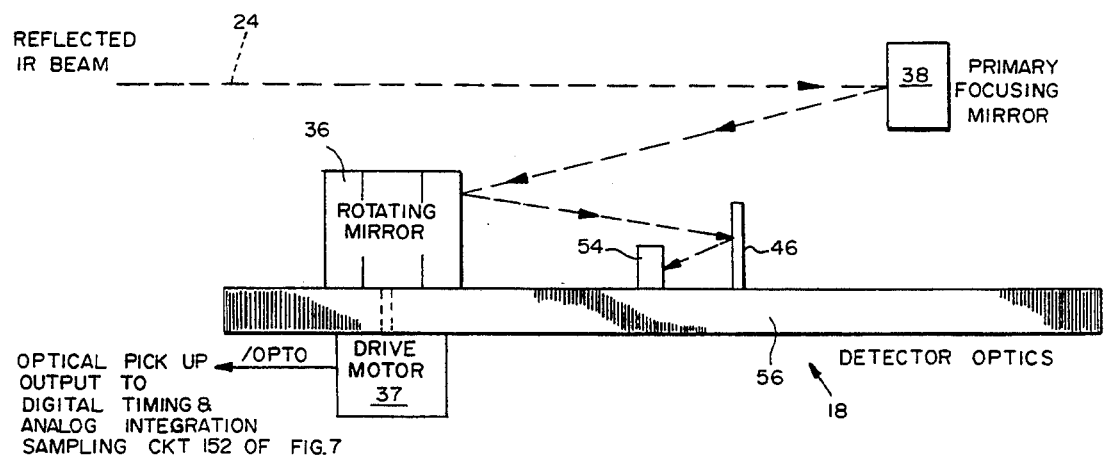
FIG. 4 is a side elevation view of the detector optics arrangement shown in FIG. 3.

Referring to FIG. 3, there is shown a plan view of the detector optics module 18 within the gas analyzer 12. A side elevation view of the detector optics module 18 is shown in FIG. 4. As shown in the figures, the reflected IR beam 24 is directed into the detector optics module 18 and onto a concave primary focusing mirror 38. The primary focusing mirror 38 reflects the IR beam 24 downward and onto a multi-sided rotating mirror 36. As shown in FIG. 3, rotating mirror 36 is rotationally displaced in a counter-clockwise direction and reflects the IR beam in a sequential manner onto first, second, third and fourth concave secondary mirrors 40, 42, 44 and 46. The concave secondary mirrors 40, 42, 44 and 46 are arranged in a semi-circular, horizontally aligned, spaced array for focusing the IR beam onto respective IR detectors. Thus, the first, second, third and fourth concave secondary mirrors 40, 42, 44 and 46 respectively reflect and focus the IR beam onto a CO detector 48, a HC detector 50, a $CO_2$ detector 52 and a reference detector 54. IR beam 24 is reflected onto each of the concave secondary mirrors in a sequential manner, beginning with the fourth mirror 46 and ending with the first mirror 40. In an actual embodiment, the detector optics module 18 is designed to receive an IR beam 24 on the order of 4 inches square and to concentrate "pulses" of that light on the detectors. This is accomplished in an actual embodiment by means of a 3 inch primary concave mirror 38, a 12,000 RPM rotating mirror 36 comprised of a 12 faceted polygon and driven by a motor 37, and four 38 mm concave secondary mirrors 40, 42, 44 and 46. This provides a pulse frequency of the IR beam on each detector of 2,400 pulses per second. Each of the detectors is comprised of lead sulfide or lead selenide in a preferred embodiment. The IR beam is thus sequentially directed onto the fourth, third, second and first concave secondary mirrors 46, 44, 42 and 40 in this order. Drive motor 37 provides an output signal /OPTO representing the speed of rotation of the spinning mirror 36. The /OPTO signal is provided to a digital timing and integration sampling circuit described below for high speed sampling of the detected IR signal.

Figure 5:
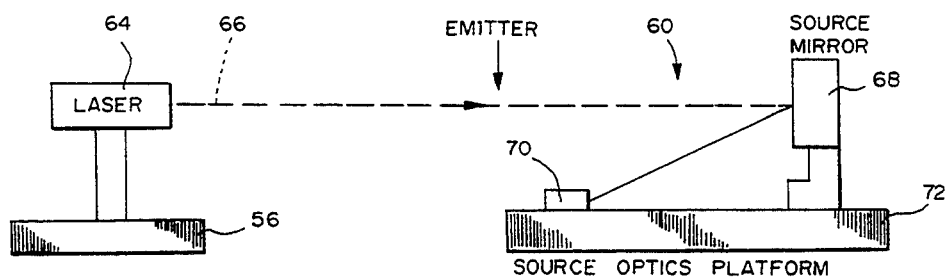
FIG. 5 is a simplified schematic diagram of an arrangement for aligning beam source optics in the remote sensor device of the present invention during manufacture.

Referring to FIG. 5, there is shown a simplified schematic diagram of an arrangement for aligning the source optics and detector optics during manufacture. A laser beam generator 64 is mounted to the detector base 56. Laser beam 66 is directed onto a source mirror 68 within the beam source optics 60. Source mirror 68 reflects the laser beam 66 onto an IR source 70. The IR source 70 and source mirror 68 are mounted to a source optics platform 72. Laser 64 is positioned at the same elevation above the detector base 56 as the previously described primary focusing mirror 38 shown in FIG. 4. If the beam source optics 60 are aligned correctly, laser beam 66 will strike the IR source 70 midway between its top and bottom portions and halfway along its length. The IR source 70 as well as source mirror 68 may be translationally displaced and/or rotated for proper alignment of the beam source optics 60 with laser beam 66. With the beam source optics 60 properly aligned, an IR beam emitted by IR source 70 and reflected by source mirror 68 will be incident upon the primary focusing mirror 38 within the detector optics module 18 for focusing on the various IR detectors as described above.

Figure 6:
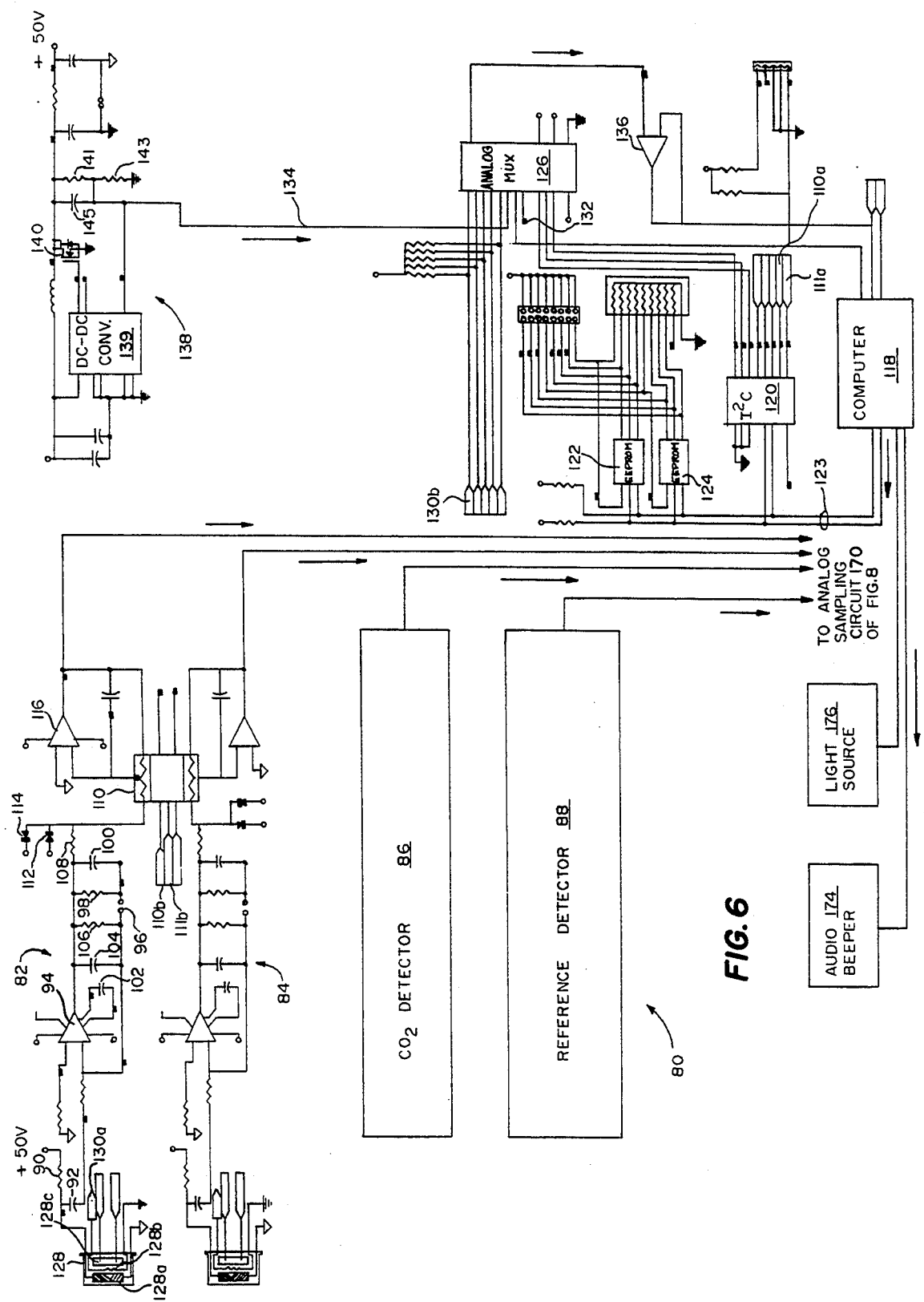
FIG. 6 is a combined schematic and block diagram of an IR detector circuit used in the remote sensor device of the present invention.

Referring to FIG. 6, there is shown a combined block and schematic diagram of an IR detector 80 used in the remote sensor device of the present invention. The IR detector 80 includes a CO detector circuit 82, an HC detector circuit 84, a $CO_2$ detector circuit 86, and a reference detector circuit 88. Details of the CO and HC detector circuits 82, 84 are shown in the figure, with the $CO_2$ and reference detector circuits 86, 88 shown simply as blocks, it being understood that all of the detector circuits have essentially the same composition and operate in the same manner. The CO and HC detector circuits 82, 84 share a common computer controlled potentiometer 110 and operate in essentially the same manner, with details of the operation of only the CO detector circuit set forth herein for simplicity. The $CO_2$ and reference detector circuits 86, 88 similarly share a common computer controlled potentiometer, which is not shown in the figure for simplicity.

The CO detector circuit 82 is energized by a DC power supply 138 which includes a DC-to-DC converter 139 and a field effect transistor (FET) 140. Resistor 90 in series with a 50 VDC input biases the CO detector element 128. Capacitor 92 DC isolates the signal. The CO detector circuit 82 further includes an CO detector element 128 whose resistivity changes with temperature. Thus, as the temperature of the CO detector element 128 decreases, its resistance increases. CO detector element 128 includes a lead salt detector element 128a, a thermistor 128b and a thermoelectric cooler 128c for reducing the temperature of the detector element. Signal ground is provided to one input of a differential amplifier 94, with the output of the CO detector element 128 provided to its other input. Also coupled to the input of differential amplifier 94 are jumper terminals 96 which allow for reducing large input signal levels to the CO detector circuit 82. By connecting a shunt (not shown) across jumper terminals 96 the output from CO detector circuit 82 may be reduced to compensate for a large input signal level. A capacitor 102 coupled to differential amplifier 94 provides an offset compensation to prevent high frequency signals such as RF noise from causing the amplifier to oscillate. The combination of capacitor 104 and resistor 106 along with capacitor 100 and resistor 98 provides for high frequency filtering and gain control of the output of differential amplifier 94. These filter networks provide for high frequency roll-off and reduce the sensitivity of the CO detector circuit 82 to frequencies generally above 50 kHz. The filtered output of differential amplifier 94 is provided through resistor 108 to the computer controlled potentiometer 110.

Potentiometer 110 includes a resistor ladder network and functions as a dual computer controlled potentiometer in that it also operates with the HC detector circuit 84. Resistor 108 and clamping diodes 112 and 114 maintain the input to potentiometer 110 between plus and minus five volts so that the output of the potentiometer does not exceed predetermined limits. The output of potentiometer 110 is provided to a differential amplifier 116, the output of which is fed back to the potentiometer for gain control. With 256 resistors in potentiometer 110, the gain of differential amplifier 116 may be controlled in a step-wise fashion over plus or minus 128 increments. With the gain of differential amplifier 116 controlled by potentiometer 110, the output of the differential amplifier is provided to analog sampling circuitry described below.

IR detector 80 further includes an analog multiplexer 126 having an input pin 130b. Input pin 130b is coupled to an output pin 130a of the CO detector element 128 for providing the analog multiplexer 126 with an indication of the temperature of operation of the IR detector element. Analog multiplexer 126 is also coupled to the DC power supply 138 via a voltage feedback (VFB) line 134. The 50 VDC output from power supply 138 is divided down by the combination of a capacitor 145 and resistors 141 and 143 to provide 1.2 VDC on the VFB line 134 to the analog multiplexer 126. Analog multiplexer 126 verifies that power supply 138 is operating at 50 VDC. Input pin 132 of analog multiplexer 126 receives a /OPTO signal from the rotating mirror's drive motor 37 (FIG. 4) representing the speed of rotation of mirror 36 which signal is further provided to computer 118 via amplifier 136.

Analog multiplexer 126 provides analog output signals representing IR detector operating temperature via a voltage follower amplifier 136 to a computer 118. Computer 118 in a preferred embodiment is an 80186 microprocessor-based computer. The I²C chip 120 serves as an interface between computer 118 and potentiometer 110 and first and second electrically erasable read only memories ("EEPROMs") 122 and 124, described below. Pins 110a and 111a coupled to the I²C chip 120 are further coupled to input pins 110b and 111b, respectively, of potentiometer 110. The control input provided from computer 118 via the I²C chip 120 controls, among other things, the setting of potentiometer 110. In this manner, the amplitude of the output signal from CO detector circuit 82 representing the detected IR beam is controlled via computer 118. The output from the I²C chip 120 allows for up and down toggling of the computer controlled potentiometers within each of the respective detector circuits. In this manner, the resistance of each resistance ladder potentiometer may be precisely adjusted in a stepwise manner for precisely controlling the output signal level of the detector circuit. This ensures that the output signals from each of the gas detector circuits 82, 84, 86 and 88 are precisely adjusted to compensate for differences in the operating temperatures of the detector elements in each of these circuits.

Computer 118 also provides outputs to the aforementioned first and second EEPROMs 122 and 124. EEPROMs 122 and 124 store calibration coefficients for each of the computer controlled potentiometers from computer 118. Thus, so long as the detector circuits remain with EEPROM's 122 and 124 after calibration at the factory following manufacture, the detector module may be removed from one remote detector system and incorporated in another remote detector system, such as during trouble shooting in the field, without requiring a complicated and lengthy calibration procedure. The calibration data stored in EEPROM's 122 and 124 includes specific gas coefficients for each detector circuit.

Figure 7:
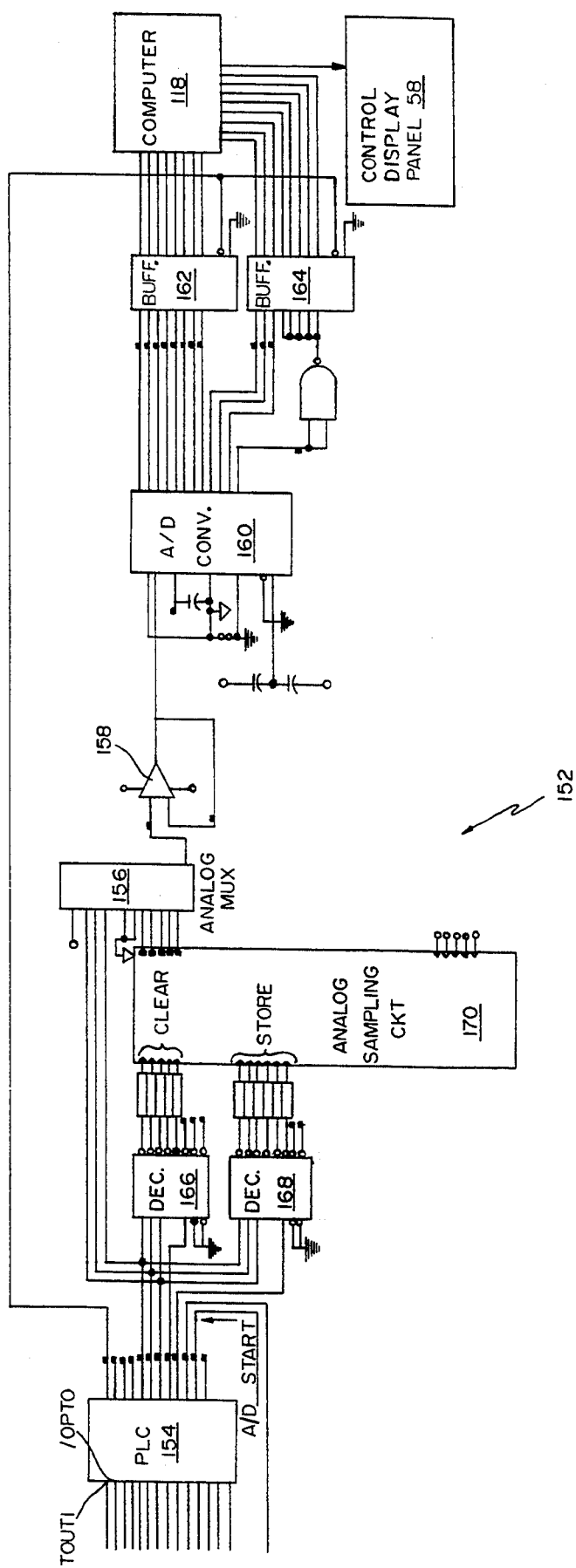
FIG. 7 is a combined block and schematic diagram of a digital timing and analog integration sampling circuit for use in the IR detector of the present invention.

Referring to FIG. 7, there is shown a combined block and schematic diagram of a digital timing and analog integration sampling circuit 152 for use in the IR detector portion of the remote sensor device of the present invention. Digital timing and analog integration sampling circuit 152 provides for high speed sampling of the detector outputs. Prior approaches in IR gas analyzers incorporating a rotating mirror arrangement provide for sampling of the gas with every two (2) revolutions of the rotating mirror. With the rotating mirror typically spinning at a speed of 12,000 RPM, the gas is sampled 6000 times per minute. The present invention employing the digital timing and analog integration sampling circuit 152 of FIG. 7 allows for sampling of the gas with each pulse provided by a respective flat of the rotating mirror. With the rotating mirror having 12 flat sides, the digital timing and analog integration sampling circuit 152 allows for sampling of the gas at a rate of 12 times 12000 RPM, or 144000 times per minute. In other words, each time an IR pulse from the rotating mirror is incident upon the detectors, the received signal is analog-to-digital converted to provide a digital representation of each received IR pulse. This extremely high rate of gas sampling minimizes the effect of noise variations in the detectors and associated circuitry for more accurate analysis of the composition of the gas. With reference to FIG. 7 as well as to the pulse diagrams of FIG. 9a and 9b, the operation of the digital timing and analog integration sampling circuit 152 will now be described.

Briefly, the digital timing and analog integration sampling circuit 152 samples the detector's output in the absence of an IR beam incident upon the detector. The sampling circuit then waits for a designated period of time as determined by the speed of rotation of the rotating mirror, and then again samples the detector and stores the sampled value on a capacitor in integrating the IR pulse received by the detector. The stored value is then analog-to-digital converted to provide a digital representation of the concentration of a pollutant in the vehicle's exhaust plume, which value is then stored.

The digital timing and analog integration sampling circuit 152 includes a programmable logic chip (PLC) 154 which receives, among other signals, a clock input TOUT1 from a master clock (not shown) and the optical pick-up output /OPTO from the drive motor 37 of rotating mirror 36. The optical pick-up signal /OPTO synchronizes operation of the digital timing and analog integration sampling circuit 152 with the high speed rotation of mirror 36, while the clock input TOUT1 synchronizes the digital timing and analog integration sampling circuit with computer 118 and other portions of the remote sensor device. Following receipt of the /OPTO input from the rotating mirror's drive motor 37, the digital timing and analog integration sampling circuit 152 counts a selected time interval, following which the IR detector circuits sample the received IR beam. The time at which the IR beam is sampled is determined by the speed of rotation of mirror 36. The /OPTO signal is provided to a programmable logic chip 154 which functions as a counter for initiating the countdown following receipt of the /OPTO input signal. After a predetermined time interval, PLC 154 provides an output to first and second decoders 166 and 168 as well as to an analog multiplexer 156. Decoders 166 and 168 provide timed store and clear inputs to an analog sampling circuit 170 described in detail below. Also provided to the analog sampling circuit 170 is the aforementioned outputs from the individual detector circuits shown in FIG. 6 and described in detail above. The outputs from the analog sampling circuit 170 representing the detected IR signals are also provided to the analog multiplexer 156. The combination of analog multiplexer 156, an operational amplifier 158 and an analog-to-digital (A/D) converter 160 convert the analog output of sampling circuit 170 to digital form. The digital outputs of the A/D converter 160 are then provided via buffers 162 and 164 to computer 118. Computer 118, in turn, provides a digital signal representing the detected IR signal to the aforementioned control/display panel 58 for display for a system operator.

The curve in FIG. 9a represents a series of pulses received by each of the detectors in the IR detector circuit of FIG. 6. The curve in FIG. 9b illustrates the integration of the received pulses shown in FIG. 9a over time by the digital timing and analog integration sampling circuit 152. With a speed of rotation of 12000 RPM, the period of received IR pulses is 416 microseconds with a 12 faceted mirror. The digital timing and analog integration sampling circuit 152 shown in FIG. 7 integrates the pulses received from each detector circuit as shown in FIG. 9b and re-zeroes, or clears, the detector circuits after receipt of an IR pulse in preparation for receipt of the next IR pulse as described below.

Figure 8:
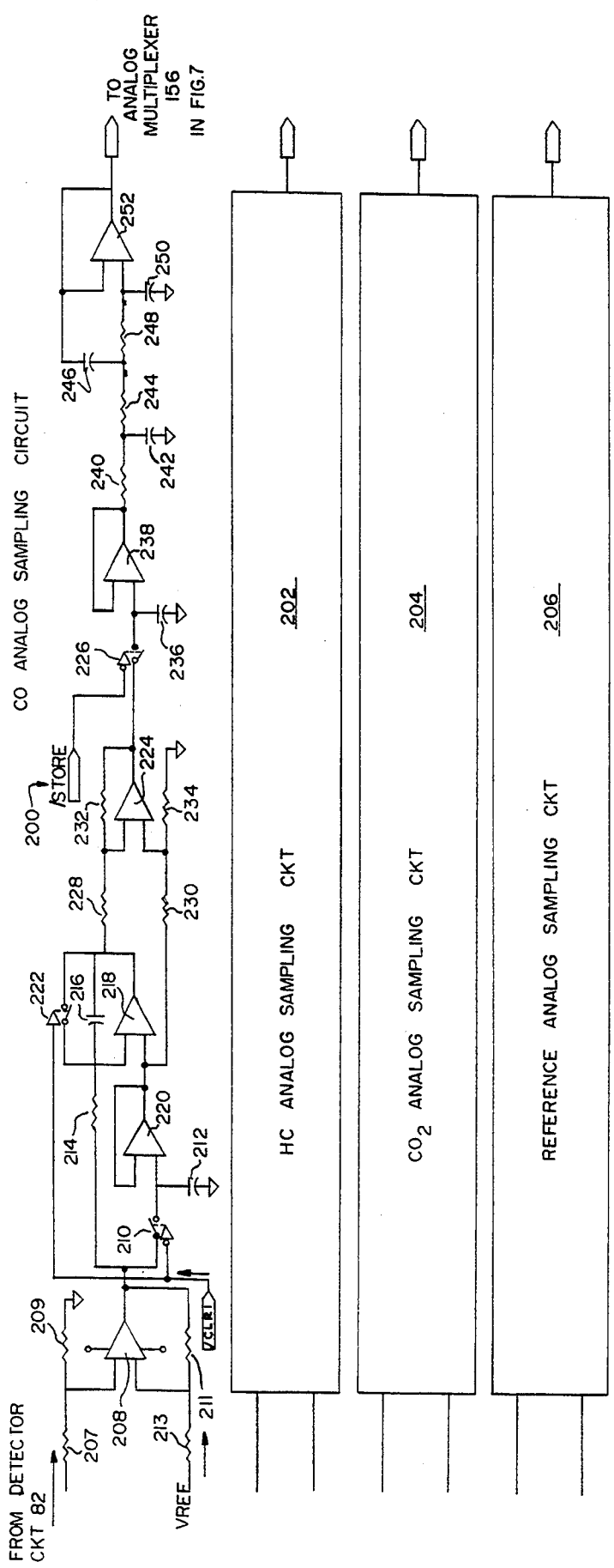
FIG. 8 is a schematic diagram of the analog portion of the sampling circuit of FIG. 7.

Referring to FIG. 8, there is shown in combined schematic and block diagram form details of the analog sampling circuit 170 of the digital timing and analog integration sampling circuit 152 of FIG. 7. As shown in FIG. 8, the analog sampling circuit 170 includes a CO analog sampling circuit 200, an HC analog sampling circuit 202, a $CO_2$ analog sampling circuit 204, and a reference analog sampling circuit 206. Details of only the CO analog sampling circuit 200 are shown in the figure for simplicity, as the remaining analog sampling circuits are similar in configuration and operation.

As shown in the upper portion of FIG. 8, two inputs are provided to a differential amplifier 208 in the CO analog sampling circuit 200 via respective voltage divider networks comprised of resistors 207, 209 and 211, 213. One input to differential amplifier 208 is the output from the CO detector circuit 82 of FIG. 6, while the other input is a reference voltage $V_{REF}$. Differential amplifier 208 operates as a voltage follower and compensates for any power or grounding problems in the input line. The output of differential amplifier 208 is provided via the combination of a solid state switch 210 and grounded capacitor 212 to one input of an operational amplifier 220. A/CLR1 input is provided to the first solid state switch 210 as well as to a second solid state switch 222 from decoder 166 as shown in FIG. 7 for clearing these switches. Solid state switch 210 is closed in the absence of an IR input to the detector, representing a zeroing of the detector. Thus, solid state switch 210 is closed for a short period, typically 10–15 microseconds, allowing capacitor 212 to charge to a level representing the detector voltage in the absence of an IR beam. Switch 210 and capacitor 212 thus operate as a sample and hold circuit, providing an input to operational amplifier 220 representing the absence of an IR input to the detector. The charge of capacitor 216 is integrated via a resistor 214 and is applied to one input of operational amplifier 218. Capacitor 216 is charged over time, such that when the charging pulse is removed, the output of differential amplifier 218 is essentially at the same level as the charge on capacitor 216. The detected IR pulse has thus been integrated as represented by the output of operational amplifiers 218 and 220 which function as a differential common mode amplifier. The integrated detected IR signal is provided from operational amplifiers 218 and 220 to operational amplifier 224 via respective networks comprised of resistors 228, 232 and 230, 234. The output of operational amplifier 224 is provided to another sample and hold circuit comprised of solid state switch 226 and grounded capacitor 236. The sample and hold circuit is updated upon receipt by switch 226 of a /STORE input from the aforementioned decoder 166 shown in FIG. 7. The output of the sample and hold circuit comprised of solid state switch 226 and capacitor 236 is provided to operational amplifier 238, the output of which is low pass filtered by means of the combination of resistors 240, 244 and 248 and capacitors 242, 246 and 250. The low pass filtered output of operational amplifier 238 is provided to operational amplifier 252 and thence to the analog multiplexer 156 in the digital timing and analog integration sampling circuit 152 as shown in previously described FIG. 7.

CO analog sampling circuit 200 operates to sample the CO detector circuit 82 for a detected IR input, temporarily store a detected IR input and then provide the IR input to computer 118 for processing and storage. Each of these operations is performed in a precisely timed manner determined by the rotational speed of spinning mirror 36. The output of the detector is sampled a predetermined time interval following detection of the absence of the IR beam on the detector, where the predetermined time interval is determined by the rotational speed of the spinning mirror.

Referring to FIG. 10, there is shown a flow chart of the operations carried out primarily by computer 118 in the remote sensor device for providing either an audio or optical signal for precisely aligning the optical elements in the source and detector modules optics 16 and 18 with the LTM 14. At step 144 an analog IR signal is detected such as by the CO detector circuit 82 which is provided to the analog sampling circuit 170 shown in FIG. 8. The output of the analog sampling circuit 170 is provided to the analog multiplexer 156 which in combination with operational amplifier 158 and A/D converter 160 converts the analog IR signal to digital form, with a count N representing signal amplitude as shown in step 146. The digitized detected IR signal is then provided to computer 118 which at step 148 determines whether the count N is greater than 3000 but less than 9500. In the present invention, twenty-four A/D conversions are used to sample the detector signal and to detect a count range of from 0 to 2048 counts. The maximum number of counts with twenty-four A/D conversions per detector is 49,152 divided by 5, or 9,830. The number of counts is divided by 5 to provide an arbitrary maximum count of 9,500. A full scale count is arbitrarily set at 8500, with a 3000 count establishing the low end of the detection of an IR signal. Computer 118 therefore at step 148 compares the number of counts in the detected IR signal with, the low end limit of 3000 and the upper end limit of 9500. If the number of counts is less than 3000 or greater than 9500, an audio beeper 174 and/or a light source 176 coupled to the computer is turned off, indicating absence of a received IR signal. If at step 148 it is determined that the count of the detected IR signal is between 3000 and 9500, the program stored in computer 118 branches to step 150 and pulses the audio beeper 174 and/or light source 176 with a signal count N. The operator of the remote sensor device then adjusts the optical components of the system, such as the lateral transfer mirror, to increase the count, or pulse rate, of the audio and/or light signals until the beat frequency is maximized.

From the foregoing, it can be seen that there has been provided apparatus for detecting and measuring relative concentrations of pollutants such as HC, CO and $CO_2$ in the exhaust emissions of a passing vehicle. The apparatus employs an IR beam directed twice through the vehicle's exhaust plume using a combination IR source and detector module on one side of the roadway and a lateral transfer mirror on the other side of the roadway. The lateral transfer mirror provides a fixed, precisely defined horizontal displacement between the emitted and reflected beams which permits close spacing between the source and detector optics such as in a single module. The lateral transfer mirror includes two transversely oriented reflectors rigidly coupled by an intermediate aluminum panel which provides an integral structure which facilitates optical alignment of the apparatus. The IR detector module includes a high speed, rotating mirror arrangement for sequentially directing the reflected IR beam in a pulsed manner onto a plurality of spaced detector elements, each adapted for detecting a specific pollutant. The IR beam is sampled with each IR pulse provided to the detectors at a rate greater than the speed of rotation of the mirror which nominally operates at 12,000 RPM. This high speed sampling rate is used to calibrate each detector circuit at a high rate to minimize circuit drift and other sources of measurement inaccuracy. A pulsed output representing the detected IR signal is provided to an audio beeper and/or a visible light which are pulsed so as to indicate the strength of the received IR signal. The optical elements of the source and detector optics are adjusted until the audio beeper and/or light source provide a maximized beep and/or light pulse frequency.

I claim:

1. Apparatus for high speed detection of pollutants in an exhaust plume of a motor vehicle, wherein an IR beam is directed through said exhaust plume and interacts with said pollutants, said apparatus comprising: optical means including a rotating mirror for receiving the IR beam after transit through the exhaust plume, wherein said rotating mirror includes N reflecting side walls and rotates at an angular velocity V; a plurality of IR detectors each adapted to detect a specific pollutant in the exhaust plume, wherein said IR detectors are arranged in a spaced array adjacent to said rotating mirror and adapted to receive the IR beam reflected from the side walls of said rotating mirror, wherein the IR beam reflected from one of the side walls of said rotating mirror is sequentially directed onto each of said detectors and wherein each of said IR detectors receives said IR beam as a series of IR pulses; and digital timing means coupled to said rotating mirror and responsive to the angular velocity V thereof and further coupled to each of said IR detectors for actuating said IR detectors in a timed manner, wherein each of said IR detectors samples the IR beam upon receipt of an IR pulse at predetermined time intervals determined by the angular velocity V of said rotating mirror.

2. The apparatus of claim 1 wherein N is 12 and V is on the order of 12,000 revolutions per minute (RPM).

3. The apparatus of claim 1 wherein said rotating mirror includes a drive motor for rotationally displacing said mirror and for providing a signal representing angular velocity of said mirror to said digital timing means.

4. The apparatus of claim 1 further comprising an analog sampling circuit coupled to said digital timing means and to said IR detector for storing a charge representing an IR pulse.

5. The apparatus of claim 4 wherein said analog sampling circuit includes capacitor means for storing a charge representing an IR pulse.

6. The apparatus of claim 5 wherein said digital timing means clears said capacitor means after a predetermined time interval following receipt of an IR pulse.

* * * * *